United States Patent
Gyollai et al.

(10) Patent No.: US 7,358,093 B2
(45) Date of Patent: Apr. 15, 2008

(54) AZTREONAM L-LYSINE AND METHODS FOR THE PREPARATION AND ANALYSIS THEREOF

(75) Inventors: Viktor Gyollai, Debrecen (HU); Csaba Szabo, Debrecen (HU); Claude Singer, Kfar Saba (IL); Istvan Bodi, Balmazujvaros (HU)

(73) Assignee: Corus Pharma, Inc., Seattle, WA (US)

( * ) Notice: Subject to any disclaimer, the term of this patent is extended or adjusted under 35 U.S.C. 154(b) by 0 days.

(21) Appl. No.: 11/723,867

(22) Filed: Mar. 22, 2007

(65) Prior Publication Data

US 2007/0167424 A1  Jul. 19, 2007

(51) Int. Cl.
- *G01N 33/15* (2006.01)
- *G01N 21/94* (2006.01)
- *C07D 205/085* (2006.01)

(52) U.S. Cl. ......................................... 436/96
(58) Field of Classification Search .................. 540/355
See application file for complete search history.

(56) References Cited

U.S. PATENT DOCUMENTS

| | | | |
|---|---|---|---|
| 4,675,398 A | 6/1987 | Sedergran | |
| 6,660,249 B2 * | 12/2003 | Montgomery | 424/45 |
| 7,214,364 B2 * | 5/2007 | Montgomery | 424/46 |
| 2004/0247628 A1 * | 12/2004 | Lintz et al. | 424/400 |
| 2005/0032775 A1 * | 2/2005 | Gyollai et al. | 514/210.15 |
| 2005/0063912 A1 * | 3/2005 | Montgomery et al. | 424/46 |
| 2006/0057073 A1 * | 3/2006 | Lintz et al. | 424/45 |

FOREIGN PATENT DOCUMENTS

WO  WO 01/34128  5/2001

OTHER PUBLICATIONS

Fernandez et al., "Inhaled Aztreonam Therapy in Patients with Cystic Fibrosis Colonized with *Pseudomonas aeruginosa*" Anales Espanoles De Pediatria vol. 40 No. 3, 1994 (in Spanish).

Fernandez et al., "Inhaled Aztreonam Therapy in Patients with Cystic Fibrosis Colonized with *Pseudomonas aeruginosa*" Anales Espanoles De Pediatria vol. 40 No. 3, 1994 (Translated to Education).

* cited by examiner

*Primary Examiner*—Mark L Berch
(74) *Attorney, Agent, or Firm*—Cooley Godward Kronish LLP

(57) ABSTRACT

The present invention relates to the L-lysine salt of aztreonam and methods for making the L-lysine salt of aztreonam.

2 Claims, No Drawings

AZTREONAM L-LYSINE AND METHODS FOR THE PREPARATION AND ANALYSIS THEREOF

CROSS-REFERENCED TO RELATED APPLICATIONS

This application claims the benefit of U.S. Provisional Application Ser. Nos. 60/484,861 filed Jul. 2, 2003 and 60/550,098 filed Mar. 4, 2004 and U.S. application Ser. No. 10/882,591 filed Jul. 1, 2004, the disclosures of which are incorporated by reference in their entirety herein.

FIELD OF THE INVENTION

The present invention relates to the L-lysine salt of aztreonam and methods for making the L-lysine salt of aztreonam.

BACKGROUND OF THE INVENTION

Aztreonam is a monobactam antibiotic disclosed in U.S. Pat. No. 4,775,670, which is incorporated by reference herein in its entirety. Aztreonam has the chemical name (Z)-2-[[[(2-amino-4-thiazolyl)[[(2S,3S)-2-methyl-4-oxo-1-sulfo-3-azetidinyl]carbamoyl]methylene]amino]oxy]-2-methylpropionic acid. Aztreonam is also known as [3S-[3α(Z), 4β]]-3-[-[(2-amino-4-thiazolyl)[(1-carboxy-1-methylethoxy)imino]acetyl]amino]-4-methyl-2-oxo-1-azetidinesulfonic acid and (2S,3S)-3-[[2-[2-amino-4-thiazolyl]-(Z)-2-[(1-carboxy-1-methylethoxy)imino]acetyl]amino]-4-methyl-2-oxo-1-azetidine-1-sulfonic acid. Aztreonam has the structure:

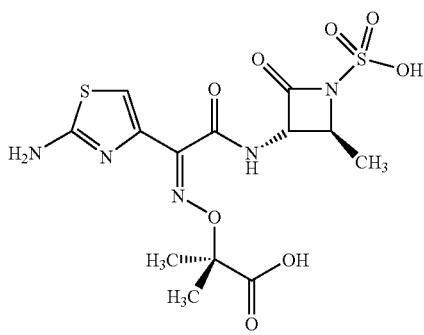

U.S. Pat. No. 4,775,670 discloses a process for making Aztreonam and pharmaceutically acceptable salts thereof. However, U.S. Pat. No. 4,775,670 does not teach how to prepare salts of Aztreonam with amines or amino acids.

Applicants encountered unexpected difficulties when trying to prepare salts of Aztreonam with amines and amino acids by dissolution of the acid and base in a solvent and precipitation of the salt. In the majority of experiments an oil, which was impossible to crystallize and which decomposed very rapidly, was obtained.

Applicants have discovered methods that enable the preparation of a solid, stable Aztreonam L-lysine salt.

SUMMARY OF THE INVENTION

The invention relates to an amorphous, solid Aztreonam L-lysine salt. The invention also relates to methods for making the amorphous L-lysine salt. The first method comprises freeze-drying an aqueous solution of Aztreonam L-lysine. The second method comprises spray-drying an aqueous solution of Aztreonam L-lysine. The third method comprises precipitating Aztreonam L-lysine from an aqueous solution.

DETAILED DESCRIPTION OF THE INVENTION

Aztreonam is converted into its L-lysine salt in aqueous solution. The pH plays an important role in the stability of the Aztreonam L-lysine aqueous solution and it should not be more than 5.5. The salt may be isolated from the aqueous solution as an amorphous solid by three different techniques. The three techniques include freeze-drying, spray-drying and precipitation in an organic solvent. All three techniques provide an amorphous product.

Aztreonam L-lysine salt may be obtained by freeze drying an aqueous solution of aztreonam L-lysine. The ratio of Aztreonam and L-lysine used to form the aqueous solution is preferably between 1:1 and 1:2.1. The product obtained by this method appears as white to yellowish flakes and contains about 3 to about 6% water.

Aztreonam L-lysine may also be obtained by spray drying an aqueous solution of Aztreonam L-lysine. The Aztreonam L-lysine salt obtained by spraying is a white to off-white powder. The water content of the product obtained by this method is between about 4 to about 7%. The preferred spray drying parameters are listed in the following table. The parameters apply to a Buchi laboratory spray-drier B-191 (Aspirator rate: 31.5 m$^3$/h).

| Pump speed (ml/h) | Inlet temperature (° C.) | Spray flow (l/h) | Concentration of solution (m/m %) | Outlet temperature* (° C.) |
|---|---|---|---|---|
| 240 ... 750 | 115 ... 195 | 400 ... 800 | 7 ... 29 | 45 ... 127 |

*The outlet temperature depends mainly on the pump speed, inlet temperature, spray flow and concentration of solution.

Using optimal drying parameters, the product exhibited good handling properties, i.e., it was free-flowing. The particle size can also be influenced by regulating the specific drying parameters.

The L-lysine salt of aztreonam can also be isolated by precipitating Aztreonam L-lysine from an aqueous solution. The aqueous solution of aztreonam L-lysine is preferably dropped into an aqueous or anhydrous organic solvent, e.g., ethanol, acetone, etc. The water content of the alcohol used for the precipitation is preferably between about 0 and 9% (m/m).

The Aztreonam L-lysine obtained using these methods was stable in the sense that during 3 months at 2-8° C.:
1. the assay of Aztreonam was maintained constant in the limit 60-66%; and
2. no impurity exceed 0.3 area %.

EXAMPLES

The impurity content of Aztreonam lysine salt using the HPLC method is determined as follows:

a. Aztreonam Lysine salt sample is dissolved in 0.02 M KH$_2$PO$_4$ buffer solution (pH adjusted 2.0 with 25 w/w % phosphoric acid) diluent, b. The sample solution (ca. 10 μl) is injected into a 100.0 mm×4.0 mm, 3 μm RP-18 HPLC column, c. Gradient eluting with a mixture of 0.02 M $KH_2PO_4$ buffer solution (pH adjusted 3.0 with 25 w/w % phosphoric acid) (A) and acetonitrile (B) according to the following profile:

| Flow rate [ml/min] | Time [min] | Eluent A [v/v %] | Eluent B [v/v %] |
|---|---|---|---|
| 1.2 | 0.0 | 100.0 | 0.0 |
| 1.2 | 16.0 | 84.0 | 16.0 |
| 1.2 | 25.0 | 70.0 | 30.0 |
| 1.2 | 25.1 | 100.0 | 0.0 |
| 1.2 | 30.0 | 100.0 | 0 | d. The amounts of each impurity was measured at 230 nm wavelength with a UV detector and appropriate recording device.

e. The amount of each impurity was calculated referring to an Aztreonam working standard at a concentration of 2.5 g/ml.

In the above method, Aztreonam has a retention time of about 10.2 minutes.

The assay of Aztreonam Lysine salt using the HPLC method was determined as follows:

a. Dissolving Aztreonam Lysine salt sample in a mixture of 0.02 M $KH_2PO_4$ buffer solution (pH adjusted 3.0 with 25 w/w % phosphoric acid) and methanol (80:20) diluent, b. Injecting the sample solution (ca. 10 μl) into a 50.0 mm×4.6 mm, 3 μm RP-18 HPLC column, c. Isocratic eluting at 1.5 ml/min with a mixture of 0.02 M $KH_2PO_4$ buffer solution (pH adjusted 3.0 with 25 w/w % phosphoric acid) and methanol in a 83:17 v/v % ratio.

d. Measuring of the amounts of each impurity at 270 nm wavelength with a UV detector and appropriate recording device.

e. Calculating of the assay referring to the Aztreonam working standard at a concentration of 100 μg/ml.

In the above method, Aztreonam has a retention time of about 2.3 minutes

Example 1

Aztreonam (5.00 g, water content: 12.2%) was suspended in 25 ml distilled water at 0-5° C. A solution of 2.70 g L-lysine in 13.5 ml distilled water was added dropwise to the above suspension with cooling (ice-water bath). The solution of Aztreonam L-lysine salt obtained by this method was filtered on a glass filter and freeze dryed.

Product: white flakes.
Yield: 6.8 g (quant.)

Example 2

Aztreonam (35.0 g, water content: 12.6%) was suspended in 230 ml distilled water at 0-5° C. A solution of 17.5 g L-lysine in 45 ml distilled water was added dropwise to the above suspension with cooling (ice-water bath). The solution of Aztreonam L-lysine salt obtained by this method was decolorized with charcoal, filtered on a glass filter and spray dryed using laboratory spray dryer Buchi B-191.

Product: white powder.
Yield: 31 g (62%)

The Aztreonam L-lysine salt produced according to this example, does not contain any impurity exceeding 0.3 area %, and/or maintains at least about 63 weight % of the Aztreonam, after storage for three months at about 2-8° C.

Example 3

Aztreonam (3.50 g, water content: 11.3%) was suspended in 8 ml distilled water at 0-5° C. A solution of 1.80 g L-lysine in 3.5 ml distilled water was added dropwise to the above suspension with cooling (ice-water bath). The solution of Aztreonam L-lysine salt obtained by this method was diluted with 23 ml ethanol and added dropwise to the stirred mixture of 60 ml ethanol and 4.75 ml water at 0-5° C. in 15 min. 120 ml pure ethanol was added dropwise together with the Aztreonam L-lysine salt solution but from another dropping funnel in the same time period. The precipitation was filtered off and dried in air-circulated oven at 38° C.

Product: white powder.
Yield: 3.86 g (77%)

Having thus described the invention with reference to particular preferred embodiments and illustrated it with examples, those of skill in the art may appreciate modifications to the invention as described and illustrated that do not depart from the spirit and scope of the invention as disclosed in the specification.

What is claimed is:

1. A method for determining a level of impurities in an Aztreonam Lysine salt, the method comprising:

forming a sample solution by dissolving the Aztreonam Lysine salt in a $KH_2PO_4$ buffer solution, having a concentration of about 0.02 M and a pH adjusted to about 2 with about 25 weight percent phosphoric acid;

injecting the sample solution of the Aztreonam Lysine salt into a HPLC column;

eluting the injected sample with a mixture of a $KH_2PO_4$ buffer solution (A) and acetonitrile (B), wherein the buffer solution (A) has a concentration of about 0.02 M and a pH adjusted to about 3 with about 25 weight percent phosphoric acid, and the injected sample is gradient eluted; and determining the amount of each impurity by measuring at a wavelength of about 230 nm with a UV detector and referring to an Aztreonam working standard at a concentration of about 2.5 g/ml.

2. A method for determining a level of impurities in an Aztreonam Lysine salt, the method comprising:

forming a sample solution by dissolving the Aztreonam Lysine salt in a mixture of a $KH_2PO_4$ buffer solution, having a concentration of about 0.02 M and a pH adjusted to about 3 with about 25 weight percent phosphoric acid, and methanol;

eluting the injected sample at about 1.5 ml/min with a mixture of a $KH_2PO_4$ buffer solution, having a concentration of about 0.02 M and a pH adjusted to about 3 with about 25 weight percent phosphoric acid, and methanol in a volume ratio of about 83:17, and the injected sample is isocratic eluted; and the amount of the at least one impurity is measured at about 270 nm wavelength with a UV detector; and determining the amount of each impurity by measuring at about 270 nm wavelength with a UV detector and referring to an Aztreonam working standard at a concentration of about 100 μg/ml.

* * * * *

UNITED STATES PATENT AND TRADEMARK OFFICE
CERTIFICATE OF CORRECTION

PATENT NO. : 7,358,093 B2  
APPLICATION NO. : 11/723867  
DATED : April 15, 2008  
INVENTOR(S) : Viktor Gyollai et al.

Page 1 of 1

It is certified that error appears in the above-identified patent and that said Letters Patent is hereby corrected as shown below:

ON THE TITLE PAGE

After the last line of section (65) "Prior Publication Data" and before section (51) "Int. Cl.", insert a section as set forth below:

--Related U.S. Application Data

Continuation of application No. 10/822,591, filed on Jul. 1, 2004, now Pat. No. 7,262,293.

Provisional application No. 60/484,861, filed on Jul. 2, 2003.

Provisional application No. 60/550,098, filed on Mar. 4, 2004.--.

IN THE CLAIMS

At column 4, line 57, after the semicolon, delete the word "and".

Signed and Sealed this

Twenty-third Day of June, 2009

JOHN DOLL  
*Acting Director of the United States Patent and Trademark Office*